(12) United States Patent
Vincent

(10) Patent No.: US 7,985,377 B2
(45) Date of Patent: Jul. 26, 2011

(54) APPARATUS FOR MONITORING CHLORINE CONCENTRATION IN WATER

(75) Inventor: David Robert Vincent, West Moors (GB)

(73) Assignee: Intellitect Water Limited, Christchurch (GB)

( * ) Notice: Subject to any disclaimer, the term of this patent is extended or adjusted under 35 U.S.C. 154(b) by 520 days.

(21) Appl. No.: 12/224,153

(22) PCT Filed: Jan. 22, 2007

(86) PCT No.: PCT/GB2007/000188
§ 371 (c)(1),
(2), (4) Date: Aug. 18, 2008

(87) PCT Pub. No.: WO2007/096577
PCT Pub. Date: Aug. 30, 2007

(65) Prior Publication Data
US 2009/0057145 A1    Mar. 5, 2009

(30) Foreign Application Priority Data
Feb. 24, 2006 (GB) .................... 0603778.2

(51) Int. Cl.
G01N 27/00 (2006.01)
G01N 27/416 (2006.01)
(52) U.S. Cl. ............. 422/82.01; 204/416; 205/778.5
(58) Field of Classification Search .......... 204/416–418; 205/778.5; 422/82.01, 82.03
See application file for complete search history.

(56) References Cited

U.S. PATENT DOCUMENTS

| | | | |
|---|---|---|---|
| 3,966,413 A | 6/1976 | Marinenko | |
| 3,969,209 A | 7/1976 | Mueller | |
| 5,230,785 A | 7/1993 | Yager | |
| 2002/0130069 A1 | 9/2002 | Moskoff | |
| 2003/0042149 A1 | 3/2003 | Smith et al. | |

FOREIGN PATENT DOCUMENTS

| | | |
|---|---|---|
| JP | 2000-315051 | 11/2000 |
| JP | 2002-245415 | 8/2002 |
| JP | 2004 223419 A | 8/2004 |
| JP | 2005-84871 | 3/2005 |
| JP | 2005-96726 | 4/2005 |

OTHER PUBLICATIONS

JPO machine-generated English language translation of Fuji et al. JP 10-309583 A downloaded Mar. 11, 2011.*
JPO machine-generated English language translation of Takagi et al. JP 2004-223419 A downloaded Mar. 11, 2011.*
JPO English language abstract for JP 2004-166175 downloaded Mar. 13, 2011.*
JPO English language abstract for JP 2002-298116 A downloaded Mar. 13, 2011.*
JPO English language abstract for JP 11-045317 A downloaded Mar. 13, 2011.*
JPO English language abstract for JP 10-107531 A downloaded Mar. 13, 2011.*
JPO English language abstract for JP 2000-315051 A downloaded Mar. 13, 2011.*

* cited by examiner

*Primary Examiner* — Alex Noguerola
(74) *Attorney, Agent, or Firm* — Iandiorio Teska & Coleman

(57) ABSTRACT

Apparatus (2) for monitoring chlorine in water (4), which apparatus (2) comprises a flow cell (6), the flow cell (6) containing a chlorine sensor (62) and an automatic calibration system, and the automatic calibration system being such that it comprises a small pair of in-line electrodes (50) for generating low concentrations of free chlorine, and injection means (44) for injecting in use of the apparatus a salt solution (64) of known concentration.

20 Claims, 3 Drawing Sheets

APPARATUS FOR MONITORING CHLORINE CONCENTRATION IN WATER

This application is a 371 of PCT/GB2007/000188, filed Jan. 22, 2007, which claims foreign priority from United Kingdom Patent Application No. 0603778.2, filed on Feb. 24, 2006.

This invention relates to apparatus for monitoring chlorine concentration in water. More especially, this invention relates to apparatus which is for monitoring chlorine concentration in water and which has an automatic calibration system. The apparatus may be portable or structure-mounted.

Chlorine is used to disinfect and preserve drinking water throughout the world. Chlorine is expensive to manufacture, and concentrations of the chlorine in potable water must be controlled accurately in order to maintain quality. Under dosing does not provide protection. Over dosing can generate unhealthy disinfection by-products, and taste and odour complaints. As public awareness of water quality increases, and water security become a concern, monitoring of water quality, including the chlorine concentration, is becoming more common. In order to facilitate the installation of more chlorine monitors, it is necessary to employ a user-friendly calibration system.

Presently known calibration systems are unreliable and inaccurate when operated by non-specialists and occasional operators such as will often be the case, for example in building monitoring, or in aircraft and leisure facilities. The known calibration systems use chemical reagents, some of which are toxic. It is not possible to use a reference chlorine concentration, since chlorine is unstable and the concentration decays over time. One known calibration system uses calibration solutions that have been made in-situ by mixing high concentration hypochlorite with clean water in a fixed ratio. The amount of chlorine concentration decay in the concentrate is calculated from the conductivity of the mix, but this still requires storage and regular replacement of concentrated hypochlorite solution, which may not be convenient in many situations, for example in buildings or in aircraft. Another known calibration system uses hypochlorite which is generated by electrolysis. This known calibration system is large and unwieldy. Furthermore, it generates significant quantities of hydrogen gas, which is undesirable because the hydrogen gas can form part of an explosive gas mixture which can be generated if the apparatus with this known calibration system is used in a confined space.

It is an aim of the present invention to obviate or reduce the above mentioned problems.

Accordingly, in one non-limiting embodiment of the present invention there is provided apparatus for monitoring chlorine in water, which apparatus comprises a flow cell, the flow cell containing a chlorine sensor and an automatic calibration system, and the automatic calibration system being such that it comprises a small pair of in-line electrodes for generating low concentrations of free chlorine, and injection means for injecting in use of the apparatus a salt solution of known concentration.

The apparatus of the present invention is advantageous in that it enables regular calibration checks to be made without dangerous chemicals. By keeping the concentration of chlorine low, hydrogen gas liberation is also minimised to safe levels, within the solubility of hydrogen in water. The elimination of significant quantities of hydrogen gas is advantageous in helping to prevent a hazard through producing an explosive gas mixture if the apparatus is used in a confined space.

The apparatus of the present invention can be used to maintain a low-chlorine concentration where there is no fresh sample flow, keeping sensors clean and ready for use either in intermittent applications (such as aircraft) or in portable units.

The electrodes are in-line, i.e. the electrodes are in the same sample volume as the chlorine sensor. Because the electrodes are in the line of flow, it is not necessary to generate a concentrated chlorine solution externally. With the apparatus of the present invention it is possible to generate the chlorine in the same sample volume as the chlorine sensor.

Examples of standard salt solutions are those available from VWR International and called sodium chloride solution 18% weight/volume*2.51, Part Number 230386M, or sodium chloride 5M sterile solution 1*500 ml, Part Number AMREE529-500.

The calibration system may have a facility for programming in the concentration. The calibration system may then use the accuracy of the concentration of the standard salt solution to help control the calibration process.

The pair of in-line electrodes may be such that each electrode is a 4.5 mm square printed platinum electrode on an inert sintered alumina substrate, mounted onto a plastics body for integration into the flow cell. The platinum electrode may be printed with ruthenium oxide for more efficient chlorine generation.

The apparatus may include one or more of temperature measuring means, conductivity measuring means, pH measuring means, and Redox measuring means. The apparatus may then be used to make supplementary measurements of one or more of temperature, conductivity, pH, and Redox (OXIDATION REDUCTION POTENTIAL—ORP) in order to enable a more accurate calculation of the true chlorine concentration generated.

The electrodes may be made from inert metal or rare earth metal oxide. The electrodes may be microprocessor controlled for constant current or constant voltage.

The electrodes may be a pair of similar electrodes that, with periodic polarity reversal, are self-cleaning. The electrodes may be easily replaceable, with the same mounting configuration as the sensors in the apparatus.

A buffered or an un-buffered salt solution may be used, or the sample solution may be appropriate. The buffered salt solution may be phosphate buffered saline, for example phosphate buffered saline highphosphate 1*101 (VWR International). Other buffering agents may be used such for example as tris (2-amino-2-hydroxymethyl-1,3-propanediol).

The calibration system may comprise a calibration chamber, agitation means which is in the chamber, and sample control valves for permitting recirculation of a sample past the sensors during the chlorination process. The agitation means may be a stirrer or a pump. The calibration system may alternatively or additionally include a calibration chamber which includes means for reducing the free chlorine concentration.

The apparatus may include input means for adding other solutions to aid in calibration. One of these solutions may contain ammonium as a stable salt. The ammonium may react with chlorine to form chloramine compounds. This reaction may also be used to calculate the rate of chlorine generation. The solutions may be made by maintaining a saturated solution from additions of solid soluble compound, washed by controlled amounts of sample liquid.

The apparatus may include optical sensors in the apparatus.

The apparatus may include an internal battery or a range of power inputs to facilitate installation in a wide range of locations.

The apparatus may include a microprocessor with display and keypad, or a touch-sensitive screen.

The apparatus may be one in which the apparatus is portable, and in which the apparatus includes a self-priming pump.

The self-priming primary pump may include valves that can either permit a fresh water sample to flow through the flow cell, or to recirculate a small volume of a water sample, sealed hermetically so as to prevent leaks. The measurements obtained from the apparatus of the invention may be used to make calculations about the chlorine sensor calibration process, and automatically to calibrate the chlorine sensor. The measurements and calibrations are facilitated by the small flow cell size, and the integral pump and sample control valves that permit internal circulation of sample when there is no external sample flow available or during the calibration process.

The apparatus of the invention is advantageously constructed with a small flow cell with a number of miniature water quality sensors, including the chlorine sensor. The pair of in-line electrodes which are mounted inside the flow cell may be mounted onto the same body type as the miniature water-quality sensors.

External reservoirs of stable calibration solutions may be injected and used to calibrate the chlorine generator, as well as providing a source of chloride ions for electrolysis. Other sensors in the flow cell may be used to calibrate and control this process. For example, as salt solution is electrolised to form sodium hypochlorite, the conductivity of the solution changes in a predictable way. The pH and Redox will also change as chlorine is generated and reacts with ammonium or other sources of chlorine demand in the sample.

By way of example, it is mentioned that a basic calibration process may proceed as follows. Starting from a normal measurement process, the sample control valves will close, trapping the sample inside the flow cell and recirculating with the integral pump. A controlled quantity of salt solution is injected, bringing the conductivity up to a high, set value. Excess sample is released via a pressure relief valve to waste. The electro-chlorinator in the form of the in-line electrodes is turned on and controlled in a constant current mode. The operating voltage is strongly pH and temperature dependent. The amount of chlorine generated can be calculated from the current and the Faraday equation (which describes the relationship between the total charge past through the electrodes and the moles of chlorine produced), and a second calculation may be made by the change in conductivity of the sample. The response of the chlorine sensor is measured, and the calibration coefficients of the chlorine sensor are calculated.

Although the efficiency of the electro-chlorinator in the form of the in-line chlorine generating electrodes may change over time, periodic calibration checks of the system may be performed using a standard reference method. The frequency of system checks performed on the device will be a lot lower than would normally be required for a traditional chlorine sensor.

Optical sensors may also be included in the apparatus for example for sensing water turbidity and/or colour. An additional benefit of the facility to chlorinate the flow cell sample and/or add pH controlled solution may be to periodically clean the optical surfaces and check the calibration by injecting clean (no colour or no turbidity) water into the flow cell.

The apparatus may comprise an internal battery or a range of power inputs to facilitate installation in a wide range of locations.

The apparatus may also have a microprocessor with display and keypad, or there may be a touch-sensitive screen.

The microprocessor may have facilities for driving and interrogating the sensors, chlorine generator, pumps and valves.

The apparatus of the present invention preferably has the following.

a self-contained measurement cell containing a chlorine sensor and an in-line electrochemical chlorine source.
a chloramine sensor.
a dissolved oxygen-sensing capability.
a pump or propeller.
valves that control sample flow through, or seal the flow cell such that flow recirculates inside the cell.
a number of water quality sensors.
a conductivity sensor.
a pH sensor.
a Redox sensor.
a temperature sensor.
calibration solution injectors and a means to control them.
optical sensors, possibly including turbidity and/or colour.
a microprocessor with an interface to the other components in the device.
a display with user input facility.
connectors to receive and discharge sample.
a pressure relief valve, venting to waste.
an internal battery supply.
connection to an external power supply.

Embodiments of the invention will now be described solely by way of example and with reference to the accompanying drawings in which.

Figure 1:
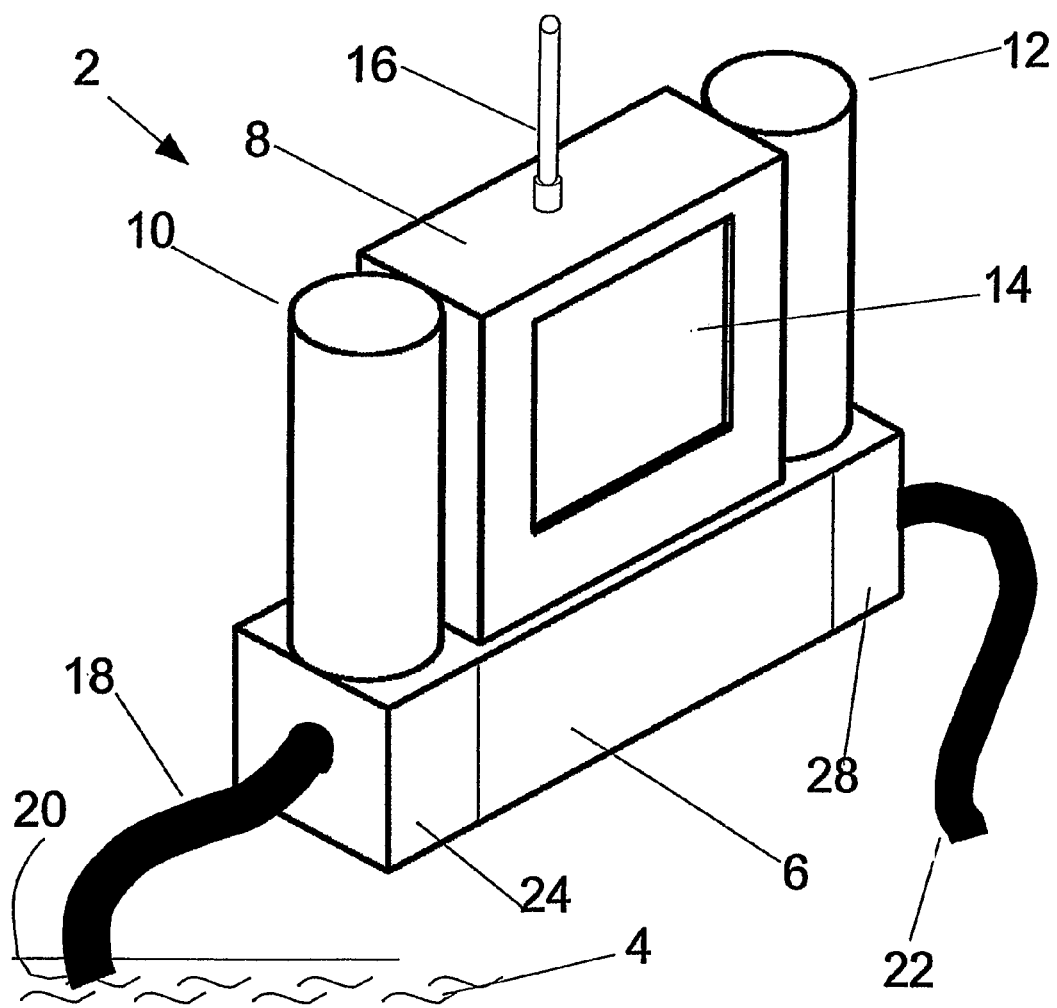
FIG. 1 is a perspective view of apparatus for monitoring chlorine concentration in water.

Referring to FIG. 1, there is shown apparatus 2 for monitoring chlorine concentration in water 4. The apparatus 2 comprises a flow cell 6 which is mounted below a housing 8 containing electronics. The apparatus 2 comprises a calibration solution container 10, and a battery container 12. The calibration solution container 10 and the battery container 12 are mounted either side of the housing 8 in order to provide easy access to the calibration solution container 10 and the battery container 12.

The electronic circuits (not shown) which are in the housing 8 are positioned behind a screen 14 which forms a touch screen local display and user interface. Results obtained from the apparatus 2 are displayed on the screen 14, as well as communicated via remote links 16 to other equipment as required.

A water sample is delivered to the apparatus 2 via a sample inlet hose 18. The sample inlet hose 18 has an end 20 placed in the water 4 which is the sample water. In an alternative embodiment not shown, the end 20 of the sample inlet hose 18 could be connected to a tap or a valve for providing the required water sample.

The apparatus 2 also comprises a sample return hose 22. This sample return hose 22 returns the sample of water back to the water 4.

A sample pump and inlet control valve are housed at an end part 24 of the flow cell 6. A sample recirculation and pressure control valve 26 is housed at an end part 28 of the flow cell 6.

Figure 2:
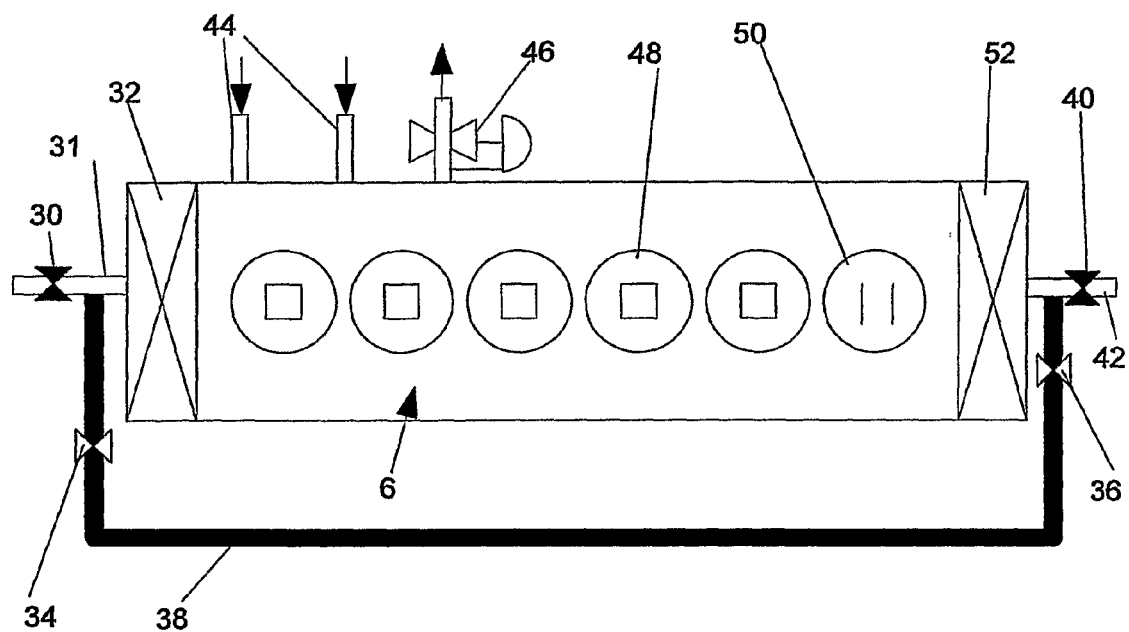
FIG. 2 shows in more detail a flow cell part of the apparatus shown in FIG. 1.

Referring now to FIG. 2, there is shown the flow cell 6. As shown in FIG. 2, the flow cell 6 is provided with an inlet valve 30 which seals a sample inlet connection 31 which connects to the sample inlet hose 18. A propeller 32 pushes the water sample through the flow cell 6. Alternatively, the water sample can be recirculated through the flow cell 6 using bypass valves 34, 36 in an open mode, whereupon the water sample is able to recirculate through a bypass conduit 38.

If an outlet valve 40 is open with the inlet valve 30, then the water sample flows out from the flow cell 12 via a connection 42 to the sample return hose 22. A propeller 52 pushes the water sample out through the outlet connection 42 when the valve 40 is open.

Injection means including ports 44 enables calibrated solutions to be injected into the flow cell 6. A pressure relief valve 46 prevents a build up of excess pressure in the flow cell 6. Sensors 48 are arranged to avoid air collecting at the top of the flow cell 6. An electrochemical generator 50 is mounted for easy servicing.

Figure 3:
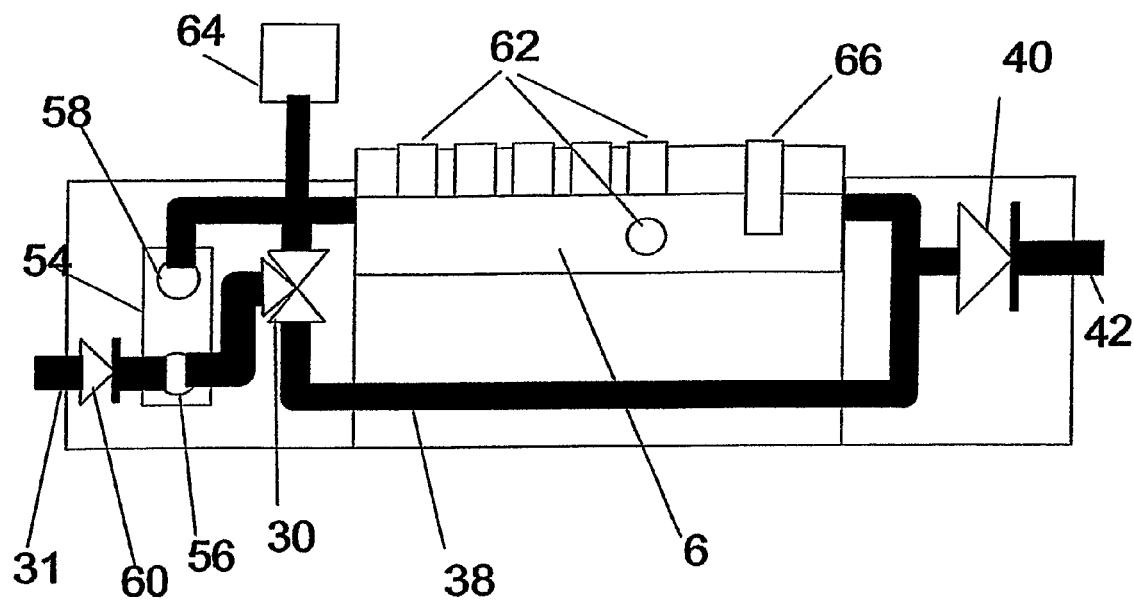
FIG. 3 shows in more detail sample control and sensing parts of the apparatus shown in FIG. 1.

Referring now to FIG. 3, there is shown sample and control sensing parts of the apparatus 2. FIG. 3 shows the flow cell 6. The flow cell 6 is able to be sealed by the outlet valve 40 which forms an exit pressure relief/non-return valve. The sealing is also effected by the valve 30 which is an inlet valve.

The apparatus 2 as shown in FIG. 3 includes a self-priming diaphragm pump 54. The pump 54 has an inlet 56 and an outlet 58. A non-return valve 60 is provided at the entrance to the inlet connection 31. When the self-priming diaphragm pump 54 is running and the inlet valve 30 is open to the sample inlet connection 31, then the sample water 4 is pumped into the flow cell 6. Release of this sample water 4 from the flow cell 6 occurs at a pressure determined by the valve 40 acting as an exit pressure relief/non-return valve. As shown in FIG. 3, the water sample is released through the valve 40 and the connection 42 for return as indicated in FIG. 1, or to a waste drain (not shown). When a fresh water sample is pumped through the flow cell 6 in this manner, sensors 62 mounted in the flow cell 6 measure their respective water quality parameters.

In order to achieve calibration, the self-priming diaphragm pump 54 continues to run, but the inlet valve 30 operates as a 3-way inlet valve 30. The inlet valve 30 redirects the sample from the exit connection 42 back to the self-priming diaphragm pump 54, via the bypass conduit 38 which acts as a recirculation loop. Since no fresh water sample 4 is being drawn into the flow cell 6, the exit or outlet valve 40 closes as the internal pressure drops. A controlled quantity of calibration solution 64 is then pumped into the flow cell 6. The quantity of the calibration solution 64 pumped into the flow cell 6 may be controlled by monitoring the conductivity using a conductivity sensor, which would be one of the sensors 62. Alternatively, the quantity of the calibration solution 64 pumped into the flow cell 6 may be controlled by pumping in a fixed volume.

The pressure increase in the water sample volume is due to the pumping in of the calibration solution 64. This pressure increase opens the outlet valve 40 and excess sample is released to waste. After the calibration solution 64 has been pumped into the flow cell 6, the conductivity is allowed to stabilise, and other water quality measurements are made in order to establish the initial state of the calibration solution.

The chlorine calibration process requires a set concentration of chlorine. This set concentration of chlorine is generated by electrolysis using a small pair of in-line chlorine generator electrodes 66. In order to maintain a stable concentration during the calibration process, it is necessary to generate sufficient chlorine in the calibration sample volume to use up the chlorine demand due to organic and other contamination in the flow cell 6 and in the sample solution 4. Current is passed through the electrode 66 for a predetermined time, and the chlorine concentration is measured using a chlorine sensor, which will be one of the sensors 62. After the current to the in-line electrodes 66 is turned off, the chlorine concentration is monitored. If the decaying concentration over a period is excessive, more chlorine is generated via the in-line electrodes 66.

The above process is repeated until it is possible to maintain a stable concentration of chlorine in the flow cell 6. This concentration of chlorine in the flow cell 6 is likely to be in the region of 1-2 mg/1. Having generated and calculated a known concentration of chlorine, using the current passed, changing conductivity and other factors, it is possible to measure the output of the chlorine sensor 8 in response to two or more chlorine concentrations. With this data, it is possible to perform a complete calibration of the calibration part of the apparatus 2.

One way of performing a complete calibration of the apparatus 2 is to add an ammonium salt solution, which is stable. A known concentration of this ammonium salt solution can be added to the chlorinated sample, reducing the free concentration by a set amount, and increasing the concentration of mono-chloramine by a similar amount. Ammonium reacts with chlorine to form mono-chloramine, which is a stable chemical and is also detected by one of the sensors in the apparatus. Once the chlorine has reacted with ammonium, it is no longer detected by the chlorine sensor, causing in a drop in this signal equal to the concentration of ammonium added. Once a concentration of chlorine has been established, the concentration of ammonium added can be used as a calibration reference for the sensitivity of the chlorine sensor. In this case, the increase in mono-chloramine measured by the mono-chloramine sensor should match the decrease in the chlorine sensor signal, and both of these values should correspond with the amount of ammonium added. This is another method of calibration using the apparatus. In each case, this is only possible because of the small volume of the apparatus 2 and in particular the small volume of the flow cell 6 and the sensors 62, and further by the number of sensors 62 available. The concentration required of chemicals and chlorine determines the amount of solution required for storage with the unit. A small volume facilitates this.

Figure 4:
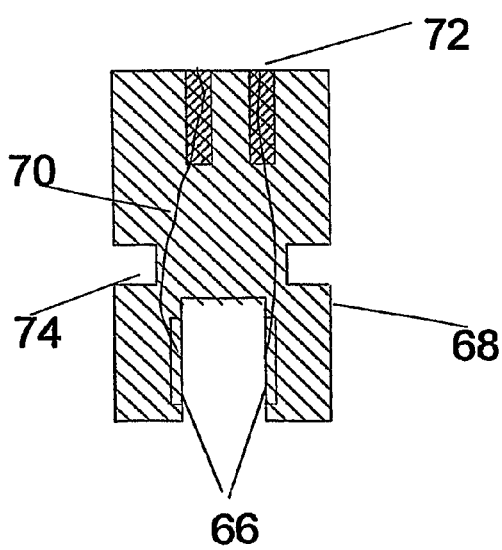
FIG. 4 shows an arrangement for mounting a small pair of in-line electrodes for generating low concentrations of free chlorine.

Referring now to FIG. 4, there is shown a simple arrangement for mounting a pair of suitable thick-film printed electrodes 66 in a small plastic body 68. The electrodes 66 are connected by a pair of wires 70 to connectors 72 at the back of the body 68. A seal is able to be achieved using O-rings (not shown) placed in a groove 74 for receiving the O-rings.

The electrode gap between the electrodes 66 is typically in the range of 1-3 mm. The electrodes 66 are preferably 4 mm×4 mm. The plastic body 6 may have an overall body diameter of typically 8 mm.

The drawings illustrate that the use of the in-line electrodes enables the apparatus of the present invention to be produced in a small and self-contained form. This permits reduced power consumption, for example by small pumps and valves. It also permits improved portability and usability of the apparatus.

It is to be appreciated that the embodiments of the invention described above with reference to the accompanying drawing have been given by way of example only and that modifications may be effected.

The invention claimed is:

1. Apparatus for monitoring chlorine in water, which apparatus comprises a flow cell, the flow cell containing a chlorine sensor and an automatic calibration system, and the automatic calibration system being such that it comprises a small pair of in-line electrodes for generating low concentrations of free chlorine, and injection means for injecting in use of the apparatus a salt solution of known concentration.

2. Apparatus according to claim 1 in which the salt solution is a buffered salt solution.

3. Apparatus according to claim 2 in which the buffered salt solution is a phosphate buffered salt solution.

4. Apparatus according to claim 1 in which the salt solution is un-buffered.

5. Apparatus according to claim 1 in which the small pair of in-line electrodes is such that each electrode is a 4.5 mm square printed platinum electrode on an inert sintered alumina substrate, mounted on a plastics body for integration in to the flow cell.

6. Apparatus according to claim 1 and including temperature measuring means.

7. Apparatus according to claim 1 and including conductivity measuring means.

8. Apparatus according to claim 1 and including pH measuring means.

9. Apparatus according to claim 1 and including Redox measuring means.

10. Apparatus according to claim 1 in which the electrodes are made from inert metal, rare earth metal oxide, or precious metal.

11. Apparatus according to claim 1 in which the electrodes are microprocessor controlled for constant current or constant voltage.

12. Apparatus according to claim 1 in which the electrodes are a pair of similar electrodes that, with periodic polarity reversal, are self-cleaning.

13. Apparatus according to claim 1 in which the electrodes are easily replaceable, with the same mounting configuration as the sensors in the apparatus.

14. Apparatus according to claim 1 in which the calibration system comprises a calibration chamber, agitation means in the chamber, and sample control valves for permitting recirculation of a sample past the sensors during the chlorination process.

15. Apparatus according to claim 14 in which the agitation means is a stirrer or a pump.

16. Apparatus according to claim 1 in which the calibration system includes a calibration chamber which includes means for reducing the free chlorine concentration.

17. Apparatus according to claim 1 and including input means for adding other solutions to aid in calibration.

18. Apparatus according to claim 1 and including optical sensors in the apparatus.

19. Apparatus according to claim 1 and including at least one of (i) an internal battery or a range of power inputs to facilitate installation in a wide range of locations, and (ii) a microprocessor with display and keypad, or a touch-sensitive screen.

20. Apparatus according to claim 1 in which the apparatus is portable, and in which the apparatus includes a self-priming pump.

* * * * *